United States Patent [19]

Georgi

[11] Patent Number: 5,610,331
[45] Date of Patent: Mar. 11, 1997

[54] THERMAL IMAGER FOR FLUIDS IN A WELLBORE

[75] Inventor: Daniel T. Georgi, Houston, Tex.

[73] Assignee: Western Atlas International, Inc., Houston, Tex.

[21] Appl. No.: 456,939

[22] Filed: Jun. 1, 1995

[51] Int. Cl.$^6$ .............................. E21B 47/00; E21B 47/10; G01F 1/74; G01K 13/00
[52] U.S. Cl. ..................... 73/152.18; 73/152.42; 73/861.04; 166/64; 166/250.01
[58] Field of Search ........................... 73/152.18, 152.13, 73/152.12, 152.42, 861.04; 166/64, 250

[56] References Cited

U.S. PATENT DOCUMENTS

| | | | |
|---|---|---|---|
| 3,656,344 | 4/1972 | Johns | 73/154 |
| 3,709,032 | 1/1973 | Coles, Jr. et al. | 73/154 |
| 3,892,128 | 7/1975 | Smith, Jr. | 73/154 |
| 4,109,717 | 8/1978 | Cooke, Jr. | 166/250 |
| 4,435,978 | 3/1984 | Glatz | 73/155 |
| 4,848,147 | 7/1989 | Bailey et al. | 73/204.17 |
| 4,974,446 | 12/1990 | Vigneaux | 73/155 |
| 5,051,922 | 9/1991 | Toral et al. | 364/510 |
| 5,121,993 | 6/1992 | Carrigan et al. | 374/29 |
| 5,226,333 | 7/1993 | Hess | 73/155 |
| 5,509,474 | 4/1996 | Cooke, Jr. | 166/64 |

FOREIGN PATENT DOCUMENTS

0683304A2  11/1995  European Pat. Off. .

*Primary Examiner*—Hezron E. Williams
*Assistant Examiner*—J. David Wiggins
*Attorney, Agent, or Firm*—Richard A. Fagin

[57] ABSTRACT

An apparatus for imaging the thermal properties of fluids in a wellbore. The apparatus includes a tool mandrel adapted to traverse the wellbore. The apparatus includes temperature sensors positioned at spaced apart locations along radially extendible arms attached to the mandrel. A temperature measuring circuit connected to each one of the sensors. The apparatus includes a circuit for applying a momentary current pulse to each of the temperature sensors, for momentarily raising their temperatures. Momentary increases in the sensor temperatures are provided so that the thermal transient response of the fluid in contact with each sensor can be determined. The invention includes a method of determining the flow regime of the fluid flowing in the wellbore. The method includes the steps of measuring the temperature of fluids in the wellbore at spaced apart locations within the cross-sectional area of the wellbore, using a tool having temperature sensors positioned at spaced apart locations. The flow regime is determined by generating a temperature map of the wellbore and comparing the temperature map with temperature maps of known flow regimes. The method includes the steps of applying current pulses to the temperature sensors to momentarily raise their temperature, measuring the temperature decay at each sensor, thereby determining the thermal transient response of the fluids in contact with each sensor. A map is generated of the thermal transient response and the thermal transient response map is compared to maps of transient responses in known fluid flow regimes.

14 Claims, 4 Drawing Sheets

THERMAL IMAGER FOR FLUIDS IN A WELLBORE

BACKGROUND OF THE INVENTION

1. Field of the Invention

The present invention is related to the field of electrical logging instruments used for evaluating wellbores drilled through earth formations. More specifically, the present invention is related to instruments used to determine the quantities and types of fluids flowing through wellbores.

2. Description of the Related Art

Wellbores drilled into petroleum reservoirs within earth formations for the purpose of extracting oil and gas typically produce the oil and gas from one or more discrete hydraulic zones traversed by the wellbore. When a wellbore is completed the zones are hydraulically connected to the wellbore. The oil and gas can then enter the wellbore, whereupon they can be transported to the earth's surface entirely by energy stored in the reservoir, or in combination with various methods of pumping.

Hydraulic zones penetrated by some wellbores can traverse a substantial length. In other wellbores a plurality of zones can be simultaneously hydraulically connected to the wellbore. In such cases, for the wellbore operator to maximize the efficiency with which the oil and gas are extracted from the reservoir it is useful to determine the rates at which oil, gas and other fluids such as water enter the wellbore from any particular point along the length of any particular hydraulic zone.

Various instruments are known in the art which can be used to determine the rates at which the fluids enter the wellbore from any particular point within any hydraulic zone. The instruments known in the art for determining the rates of fluid entry into the wellbore are called production logging tools.

Production logging tools are typically lowered into the wellbore at one end of an armored electrical cable. The tools can include sensors which are responsive to, among other things, the fractional volume of water filling the wellbore, the density of the fluid within the wellbore, and the flow velocity of the fluid in the wellbore. A record is typically made, with respect to depth within the wellbore, of the measurements made by the various sensors so that calculations can be made of the volumes of fluids entering the wellbore from any depth within the wellbore.

Methods known in the art for calculating the relative volumes of fluids entering the wellbore from production logging tool measurements generally require the use of laboratory determined models of the responses of the various production logging sensors to a range of volumetric flow rates of the different fluid phases in the wellbore. All of the sensor response models known in the art are based on an assumed "flow regime" of the fluids entering the wellbore. The flow regime is a descriptive name for the manner in which any or all of the individual phases of fluids in the wellbore travel along the wellbore, the phases typically being liquid oil, gas and water. A discussion of flow regimes can be found, for example in "A Comprehensive Mechanistic Model for Upward Two-Phase Flow in Wellbores", Ansari et al, Society of Petroleum Engineers, paper no. 20630.

A drawback to the methods known in the art for calculating the relative volumes of fluids entering the wellbore is that the methods known in the art do not account for the fact that the actual flow regime in the wellbore may be different from the particular flow regime assumed in the sensor response model. The calculations of relative volumes based on an assumed flow regime can therefore be erroneous.

It is known in the art to determine the flow regime by the use of iterative calculation techniques to fit the actual production logging tool measurements to a particular flow regime and then calculate the fluid volumes after determining the flow regime. Iterative calculation techniques can be difficult and time consuming to perform, and ultimately do not determine the flow regime to a high degree of certainty.

It is an object of the present invention to provide an apparatus and method for mapping the distribution of thermal properties of the fluids within the wellbore, so that the distribution of different types of fluids and consequently the flow regime in a wellbore can be determined to a high degree of certainty.

SUMMARY OF THE INVENTION

The present invention is an apparatus for determining the distribution of thermal properties of fluids within a wellbore. The apparatus includes a tool mandrel adapted to traverse the wellbore, a plurality of temperature sensors disposed at spaced apart locations along extensible arms attached to the mandrel, and means for measuring the temperature sensed at each one of the sensors.

In a preferred embodiment of the invention, the tool includes a means for applying a current pulse to each of the temperature sensors to momentarily raise their temperatures, so that the thermal transient response of the fluid in contact with each sensor can be determined.

The present invention is also a method of determining the flow regime in a wellbore penetrating an earth formation. The method includes the steps of measuring the temperature of fluids in the wellbore at spaced apart locations within the cross-sectional area of the wellbore using a tool having a plurality of temperature sensors, and determining the flow regime by generating a temperature map of the wellbore and comparing the map with maps of known flow regimes.

A preferred embodiment of the method according to the present invention includes the steps of applying current pulses to the temperature sensors on the tool and determining the thermal transient response of the fluids in contact with each sensor. A map is generated of the thermal transient response and the transient map is compared to maps of transient response in known flow regimes.

DESCRIPTION OF THE PREFERRED EMBODIMENT

Figure 1:
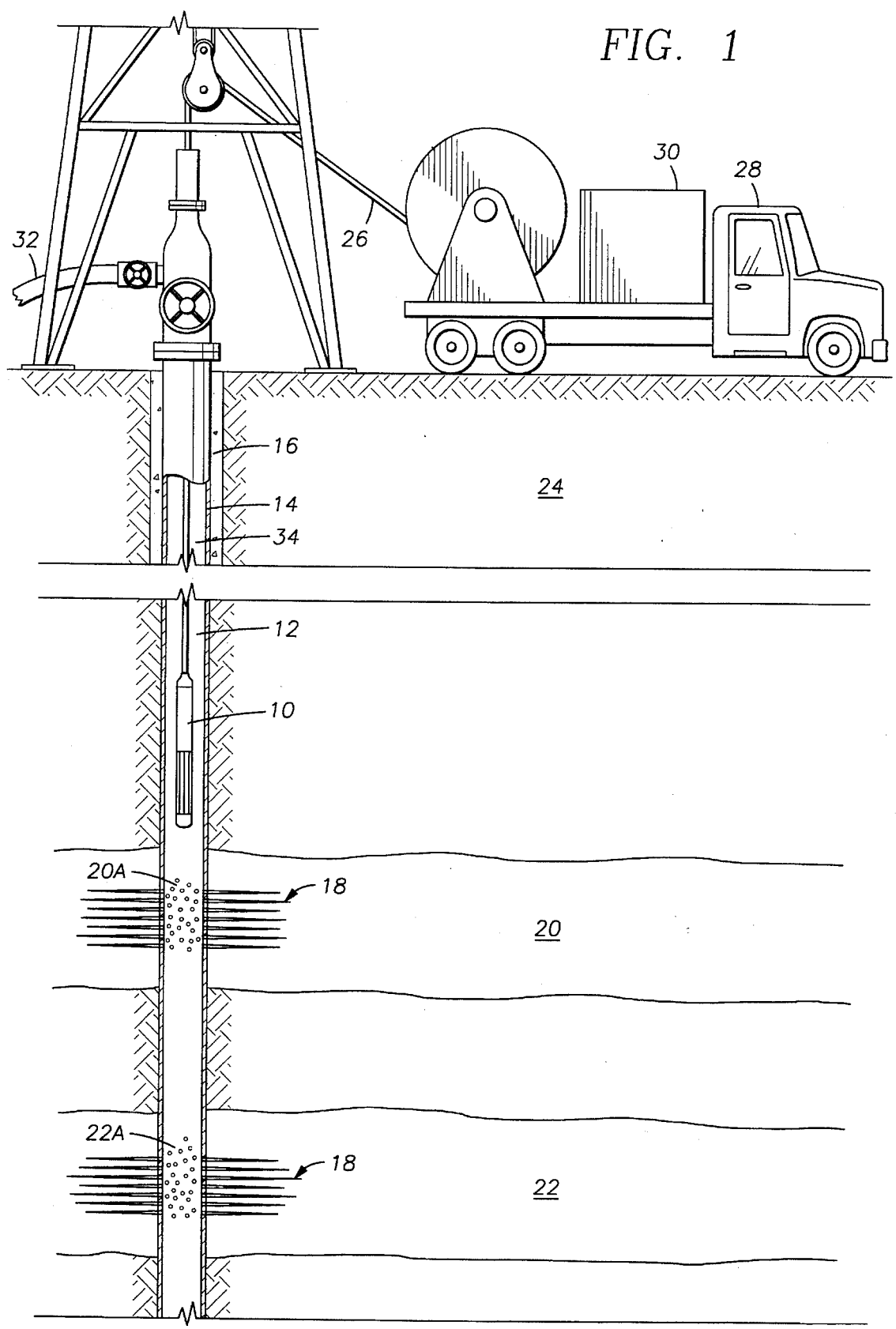
FIG. 1 shows a tool according to the present invention disposed in a wellbore.

FIG. 1 shows a logging tool 10 according to the present invention being lowered into a wellbore 12 drilled through an earth formation 24. The tool 10 is connected to one end of an armored electrical cable 26. The cable 26 can be extended into the wellbore 12 by means of a winch (not shown separately) forming part of a logging unit 28 as is understood by those skilled in the art. The other end of the cable 26 is electrically connected to surface electronics 30 also forming part of the logging unit 28. The surface electronics 30 can include a computer (not shown separately) for performing calculations on measurements made by the tool 10, as will be further explained. The tool 10 imparts signals to the cable 26 corresponding to measurements made by temperature sensors (not shown in FIG. 1 for clarity of the illustration) in the tool 10, as will be further explained. The signals imparted to the cable 26 are received and interpreted by the surface electronics 30, wherein the various temperature related measurements made by the tool 10 can be derived, as will also be further explained.

The wellbore 12 is shown penetrating a first zone 20 and a second zone 22, both of which can form part of the earth formation 24. The wellbore 12 is further shown as "completed" by having a steel casing 14 coaxially inserted therein. The casing 14 is hydraulically sealed by cement 16 filling an annular space between the casing 14 and the wellbore 12, as is understood by those skilled in the art. The first zone 20 and the second zone 22 are typically hydraulically connected to the wellbore 12 by perforations 18 made through the casing 14 and through the cement 16, as is also understood by those skilled in the art.

The first zone 20 may be spaced apart from the second zone 22 by a substantial vertical distance, and therefore can have a substantially different fluid pressure within its pore space than does the second zone 22. The pressure differential is principally caused by the earth's gravity, as is understood by those skilled in the art. The first zone 20 may also be of a different rock composition and may contain different relative volumes of oil, gas and water within its pore spaces than does the second zone 22. For these reasons and for other reasons known to those skilled in the art the fluid from the first zone 20, shown as 20A, may enter the wellbore 12 at different rates and the fluid 20A may have different fractional volumes of oil, gas and water than does the fluid entering from the second zone 22, shown as 22A. The manner in which fluid flows in the wellbore 12, called the "flow regime", can be substantially different adjacent to the second zone 22 than it is adjacent to the first zone 20, and the flow regime at either of these positions in the wellbore 12 may be substantially different than the flow regime of total produced fluid, shown at 34, which travels to the earth's surface.

The total produced fluid 34 is eventually conducted to equipment (not shown) at the earth's surface by a flowline 32 connected to the wellbore 12, wherein volumes of each of three phases of fluid, oil, gas and water, can be measured.

Figure 2:
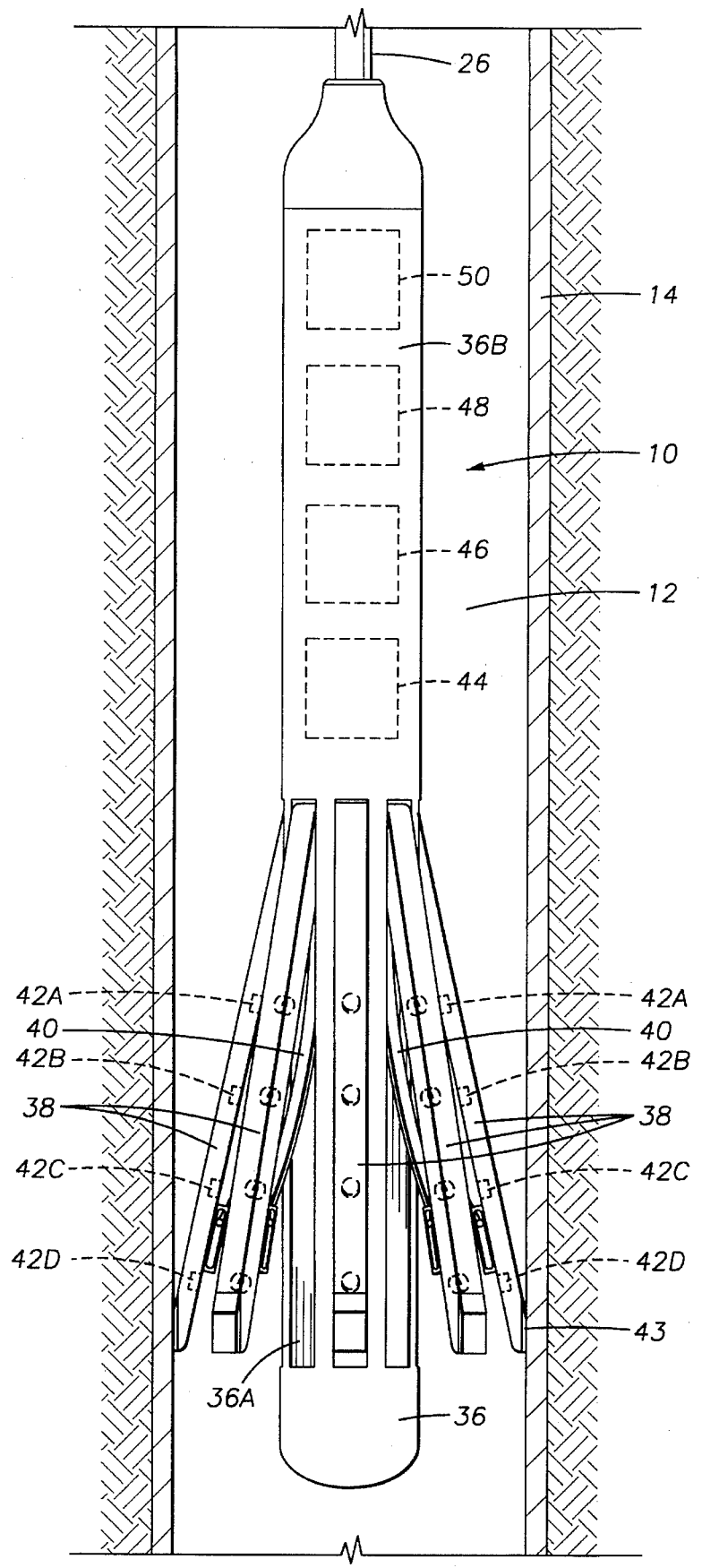
FIG. 2 shows the tool of the present invention in detail.

The tool 10 of the present invention can be better understood by referring to FIG. 2. An elongated, generally cylindrical sonde mandrel 36 can be attached to the end of the cable 26. The mandrel 36 includes an interior chamber 36B which is sealed to exclude entry of the fluid in the wellbore 12. The chamber 36B forms an enclosure for several electronic sections which will be further explained.

A lower end 36A of the mandrel 36 can consist of a highly thermally conductive material such as aluminum or brass, as will be further explained. The lower end 36A is shaped to matingly receive a plurality of sensor arms, shown generally at 38. The arms 38 can be pivotally attached to the mandrel 36 at a position where the lower end 36A joins the main body of the mandrel 36. The pivotal attachment of the arms 38 enables them to fit substantially within the mating recesses of the lower end 36A when the arms 38 are fully retracted towards the mandrel 36, and enables extension of the arms 38 so that the end of each arm, such as the one shown generally at 43, can contact the wall of the casing 14. The end 43 of each arm 38 can be formed from an abrasion resistant material such as tungsten carbide to reduce wear. The arms 38 preferably are constructed from a material having very low thermal conductivity so that temperature differences within the cross-section of the wellbore 12 are not dissipated by the arms 38. A material suitable for the arms 38 can be graphite fiber reinforced plastic.

The arms 38 can be urged into contact with the interior wall of the casing 14 by springs such as those shown generally at 40. Each arm 38 can include a means for indicating the amount of angular deflection (not shown separately for clarity of the drawing) from the closed position. Pivotal attachment means, means for urging and means for indicating the angular deflection (and consequently the amount of extension) of the arms 38 are known in the art and can include devices such as that disclosed, for example, in U.S. Pat. No. 4,121,345 issued to Roesner. The arms 38 can further include a mechanism (not shown separately) for selectively extending the arms 38 when the tool is inserted into the casing 14 to a depth of interest. Mechanisms for selectively extending and retracting the arms 38 are also known in the art and can include a mechanism such as one disclosed in the Roesner '345 patent. The pivotal attachment means, means for selectively retracting and extending the arms and the means for indicating angular deflection as disclosed in the Roesner '345 patent are meant to serve only as examples of such means. As will be appreciated by those skilled in the art, many variations of such means can be devised which will perform the same functions for the arms of the tool disclosed herein.

The means for indicating the angular deflection (not shown) of the arms 38 can be electrically connected to one of the electronic sections, shown at 44, which generates signals indicative of the angular deflection of each one of the arms 38. In the present embodiment of the invention eight such arms 38 are pivotally attached to the mandrel 36 at an angular spacing of 45 degrees between each two of the arms 38. It is contemplated that other numbers of radially spaced apart arms 38 can perform the measurements according to the present invention, and the number of arms 38 and the angular separation therebetween should not be construed as a limitation of the invention.

Typically the tool 10 is lowered into the wellbore 12 with the arms 38 fully retracted to enable relatively unrestricted movement into the wellbore 12. Upon reaching a depth in the wellbore 12 below the zones (shown as 20 and 22 in FIG. 1), the system operator can enter a command into the surface electronics (30 in FIG. 1) to extend the arms 38, and the tool 10 can be slowly pulled out of the wellbore 12 while recording, with respect to depth, the measurements made by the tool 10.

Each arm 38 includes a plurality of temperature sensors, such as those shown generally at 42A, 42B, 42C and 42D, positioned at spaced apart locations along each arm. The temperature sensors can be of a type known in the art such as thermistors. The sensors 42A–42D are each connected to a temperature measuring circuit, shown at 46, which generates a signal corresponding to the thermistor resistance, and thereby the temperature, of each sensor 42A–42D.

When the arms 38 are fully retracted, the temperature sensors 42A14 42D are positioned into contact with a wall of the lower end 36A. Because the lower end 36A is constructed from a thermally conductive material, differences in temperature across the wellbore will be dissipated within the lower end 36A, and the temperature sensors 42A–42D will each be at substantially the same temperature. The measurements made by the individual temperature sensors 42A–42D can then be normalized for small variations in response, so that small differences in temperature within the fluid in the wellbore 12 can be more accurately measured.

The tool 10 includes an electronic section including a pulsing circuit, shown at 48, which periodically electrically disconnects the temperature sensors 42A–42D from the temperature measuring circuit 46 and imparts a current pulse to each sensor 42A–42D. After the current pulse is applied to the sensors 42A–42D, the sensors 42A–42D are electrically reconnected to the temperature measuring circuit 46. The purpose of the current pulses will be further explained.

The angular deflection circuit 44 and the temperature measuring circuit 46 are connected to a data transceiver 50. The transceiver 50 imparts signals to the cable 26 corresponding to measurement signals conducted form the deflection circuit 44 and the temperature circuit 46. The transceiver 50 signals are conducted to the surface electronics (shown as 30 in FIG. 1) where the signals can be decoded and converted into temperature measurements for each sensor and angular deflection measurements for each arm 38.

As shown in FIG. 2, when the arms 38 are extended within the casing 14, each arm 38 will extend across a portion of the cross-sectional area of the casing 14 located between the mandrel 36 and the part of the wall of the casing 14 contacted by that arm 38. Because the angular deflection of each arm 38 can be determined from the measurements made from the means for determining angular deflection (not shown), and the axial position of each sensor 42A–42D on each arm 38 is known, the position with respect to the cross-section of the casing 14 of each temperature sensor 42A–42D can be determined.

Figure 3:
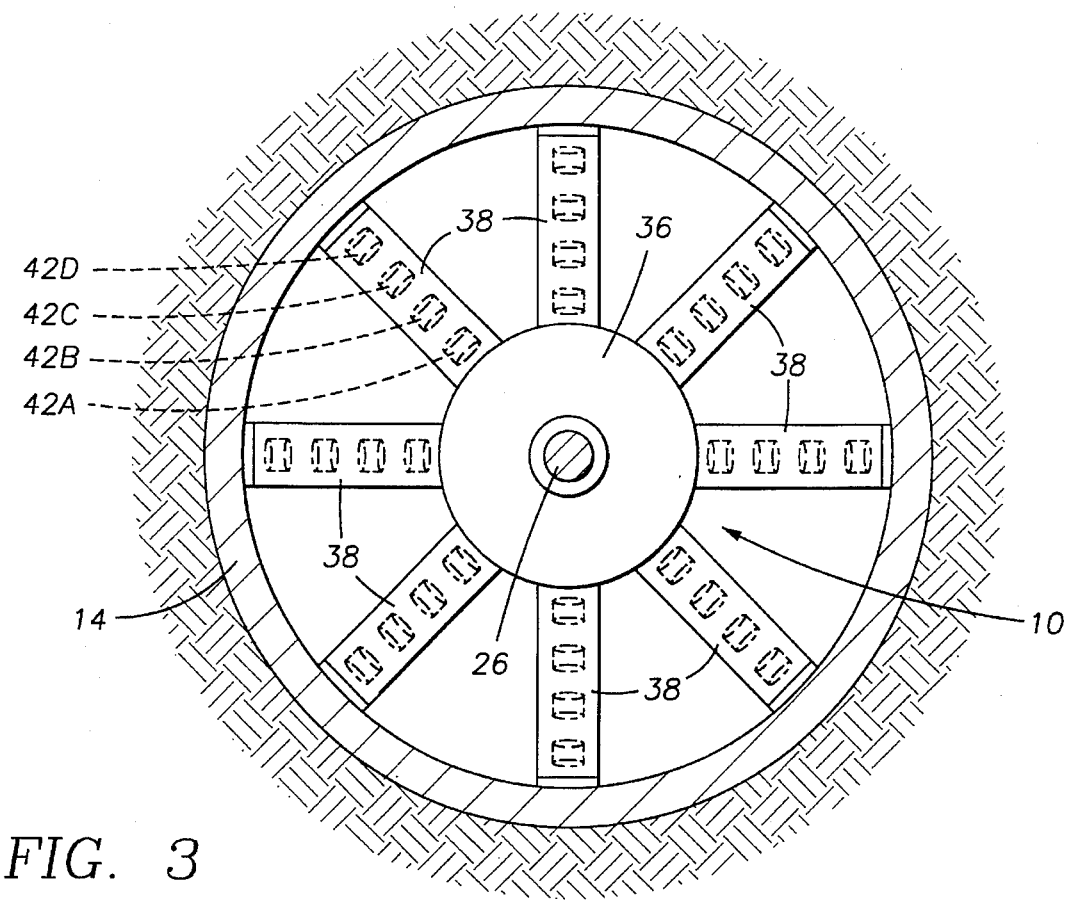
FIG. 3 shows the tool of the present invention in an end view.

The significance of determining the position of each sensor 42A–42D within the cross-sectional area of the casing 14 can be better understood by referring to FIG. 3, which is an end view of the tool 10. The mandrel 36 can be observed as positioned substantially in the center of the casing 14. The arms 38 are shown extending from the mandrel 36 outwardly to the wall of the casing 14. As can be observed in FIG. 3, the temperature sensors 42A–42D are positioned at a plurality of different positions within the cross-sectional area of the casing 14. The different positions relative to the cross-sectional area of the casing 14 can be determined because the axial position of each sensor 42A–42D is known, and the angular deflection of each arm 38 can be determined.

Figure 4:
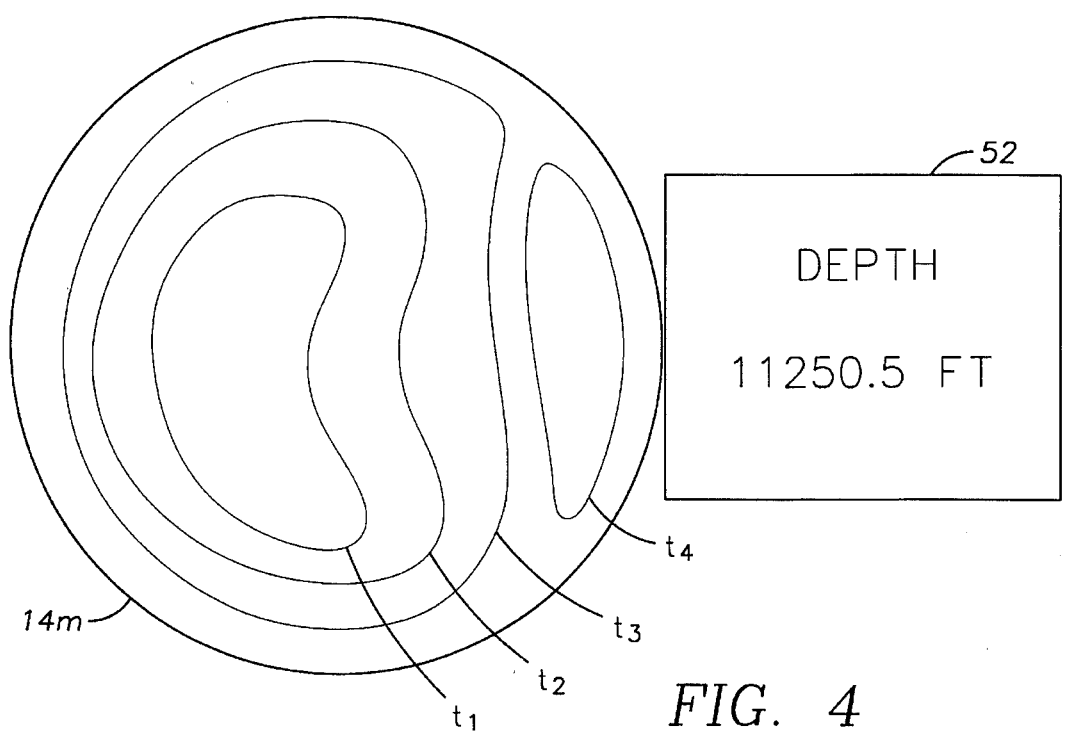
FIG. 4 shows an isothermal contour plot made from temperature measurements of the present invention.

As previously explained, the temperature measuring circuit 46 sends signals to the surface electronics (shown as 30 in FIG. 1) corresponding to the temperature at each one of the temperature sensors 42A–42D. As the tool 10 traverses the wellbore (shown as 12 in FIG. 1), temperature measurements at each sensor 42A–42D corresponding to each depth in the wellbore can be recorded. Since the position of each sensor 42A–42D within the cross-sectional area of the casing 14 can be determined, as previously explained, it is possible to construct a graphic representation, or "map", of the temperature within the casing 14 at each depth in the wellbore 12. For example, FIG. 4 shows a so-called "contour map" of temperature in the wellbore 12. The map in FIG. 4 can include an indication of the depth, as shown generally at 52, that the particular map represents. Isothermal contour lines $t_1, t_2, t_3$, and $t_4$ indicate positions within the casing of substantially equal temperature, and the contour lines can be generated from the temperature measurements corresponding to each sensor 42A–42D. The contour lines $t_1, t_2, t_3$, and $t_4$ can be generated by a computer program of a type known in the art and resident on the computer (not shown) in the surface electronics (shown as 30 in FIG. 1). The shape of the contours $t_1, t_2, t_3$, and $t_4$ can be indicative of the depth and type of fluid entry into the casing (indicated at 14M as a graphic representation on the contour plot of FIG. 4). A plurality of maps such as that shown in FIG. 4 can be generated for a plurality of different depths within the wellbore 12 in order to determine a manner in which fluid flows in the wellbore 12.

Temperature maps such as the one shown in FIG. 4 can further be used to determine whether certain ones of the perforations (shown generally at 18 in FIG. 1) are actively discharging fluid into the wellbore 12 from the producing zone adjacent thereto. For example, it is known in the art that entry of gas into the wellbore 12 is typically accompanied by a reduction in temperature due to expansion of the gas. A temperature map similar to the one shown in FIG. 4 would provide indications of temperature reduction adjacent to perforations 18 through which gas is flowing, and little or no such temperature reduction adjacent to inactive perforations 18. Ambiguities on the interpretation of a particular map ,as to whether certain perforations are active can be resolved by repeating the process of making temperature measurements and mapping the temperature when the well is restrained from producing fluid by hydraulic closure of the flow line as done with a shut in valve at the position (shown in FIG. 1 as 32), an operation known to those skilled in the art as "shutting-in" of the wellbore 2.

It is also possible, by positioning certain ones of the sensors (such as 42D in FIG. 2) at the ends 43 of the arms 38 to be in contact with the casing 14, which would enable determining whether hydraulic communication passages, called "channels", exist within the annular space between the wellbore 12 and the casing, the annular space typically being occupied by cement 16 as previously explained. Temperature differences between individual sensors 42D at the ends 43 of any of the arms 38 can be indicative of fluid movement within the annular space, thereby indicating the presence of a channel.

As previously explained, the electronic section shown at 48 in FIG. 2, called a pulsing circuit, is adapted to temporarily disconnect the sensors 42A–42D from the temperature measuring circuit 46 and apply a momentary current pulse to each sensor. The current pulse can be of variable duration, depending on, among other things, the type of sensor used. In the present embodiment of the invention, the current pulse is preferred to be of one second duration, but this duration should not be construed as a limitation of the invention. After the current pulse terminates, the pulsing circuit 48 reestablishes connection of each sensor 42A–42D to the temperature measuring circuit 46. Measurement of temperature of each sensor 42A–42D then resumes. The current pulse, however, will have slightly elevated the temperature of each sensor 42A–42D by an amount dependent on, among other things, the thermal conductivity and heat capacity of the fluid with which the sensor 42A–42D is in contact. The temperature of each sensor 42A–42D will then gradually return to the temperature of the fluid in which each sensor 42A–42D is in contact. The rate at which the temperature difference is reduced depends primarily on the thermal conductivity and the heat capacity of the fluid in which the individual sensor 42A–42D is immersed.

Figure 5:
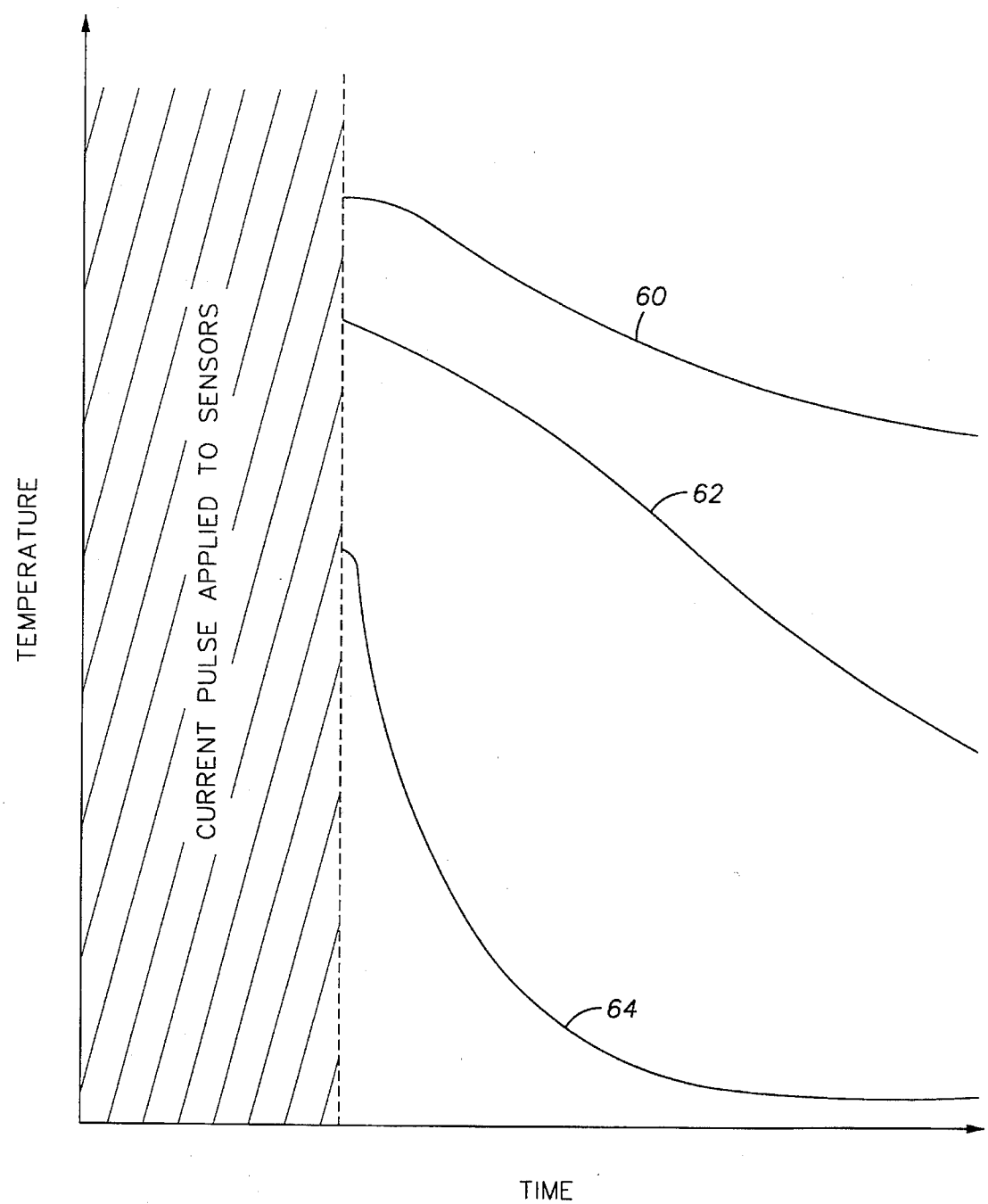
FIG. 5 shows a graph of thermal transient response for various fluids in the wellbore.

For example, FIG. 5 shows a graphic representation of sensor temperature with respect to time for a sensor immersed in gas, as shown at 60, in oil, as shown at 62, and in water, as shown at 64. Gas, typically having the lowest thermal conductivity and heat capacity of the three fluids, enables the greatest temperature increase in the sensor 42A–42D as a result of the current pulse, and provides the slowest return to the fluid temperature. Oil and water, respectively, have increasing heat capacities and thermal conductivities, and therefore provide successively smaller initial temperature increases and more rapid returns to the ambient fluid temperature. Each sensor 42A–42D can therefore provide a measurement corresponding to characteristic heat dissipation properties of the fluid in contact with that sensor 42A–42D. The heat dissipation properties of the fluid in contact with the sensor can be characterized according to the increase in sensor temperature following the current pulse and according to the rate of decrease, or decay rate, in sensor temperature following the current pulse. A system operating program resident in the computer (not shown) in the surface electronics (30 in FIG. 1) can include a routine to measure the temperature at each sensor immediately prior to and immediately after application of the current pulse to each sensor. The program can calculate the difference in the two temperature measurements. The operating program can also scan the measurements of the sensor temperature at a plurality of spaced apart time intervals following the current pulse, these time intervals preferably spaced apart at about 0.05 seconds. The program then can determine a temperature decay rate based on the plurality of spaced apart temperature measurements. The decay rate and temperature increase determined for each sensor can be compared to laboratory measurements of temperature rise and decay rate made for samples of oil, gas and water. Decay rates and temperature increases determined in the wellbore can be compared by the computer (not shown) to the laboratory measurements in order to determine the phase Composition of the fluid in contact with each sensor.

It is possible to construct a map (not shown) similar in format to the contour plot in FIG. 4 which delineates positions within the casing 14 of equal heat transfer properties. A map (not shown) of heat transfer properties can be used to determine the distribution of different fluids within the cross-section of the casing 14.

It is to be understood that the contour plot shown in FIG. 4 is only one version of "map" of the distribution of thermal properties in the wellbore 12 which can be generated using measurements from the tool 10. Many other map configurations are possible. For example, the isothermal contours $t_1$, $t_2$, $t_3$, and $t_4$ in FIG. 4 could be replaced with variable colors or gray scale shading of a type known to those skilled in the art to generate a thermal "image" of the wellbore 12.

As previously stated, it is possible to determine the physical distribution of, or to "map", the heat dissipation properties of the fluids in the wellbore 12 using the tool 10 of the present invention. By mapping the heat dissipation properties, it is possible to determine the distribution of fluids in the wellbore. The distribution of fluids in the wellbore can be used to determine the flow regime, or manner of flow of the fluids in the wellbore, by comparing the heat dissipation maps of the wellbore to maps of the heat dissipation properties of known flow regimes. Known flow regimes can be mapped by inserting the tool 10 of the present invention in a laboratory fixture known in the art as a flow-loop (not shown) and mapping the heat dissipation properties of the fluids under known fluid flow conditions.

Those skilled in the art will be able to construct improvements to the present invention without departing from the spirit of the invention disclosed herein. The invention should be limited in scope only by the claims appended hereto.

What is claimed is:

1. A method of determining a flow regime of fluids in a conduit comprising the steps of:

measuring temperature of said fluids in said conduit at known spaced apart locations within the cross-sectional area of said conduit using a tool having a plurality of temperature sensors and means for determining a position of each one of said sensors within the cross-section of said conduit;

generating a temperature map of said conduit; and comparing said map with maps of known flow regimes thereby to determine said flow regime, wherein said maps of known flow regimes are generated from laboratory experiments in a flow loop.

2. The method as defined in claim 1 wherein said step of generating a temperature map comprises generating an isothermal contour plot.

3. The method as defined in claim 1 wherein said step of generating a temperature map comprises generating an isothermal color plot.

4. The method according to claim 1 further comprising the steps of:

applying current pulses to said temperature sensors to momentarily raise the temperature of said sensors;

measuring the thermal transient response at each sensor, thereby determining heat transfer properties of fluid with which each one of said temperature sensors is in contact;

generating a map of said heat transfer properties with respect to position within the cross section of said conduit; and comparing said map to maps of heat transfer properties of fluid flowing in known flow regimes thereby determining said flow regime in said conduit, wherein said maps of known flow regimes are generated from laboratory experiments in a flow loop.

5. The method as defined in claim 4 wherein said step of generating a temperature map comprises generating an isothermal contour plot.

6. The method as defined in claim 4 wherein said step of generating a temperature map comprises generating an isothermal color plot.

7. A method of determining a flow regime of fluids in a conduit comprising the steps of:

measuring temperature of said fluids in said conduit at known spaced apart locations within the cross-sectional area of said conduit using a tool having a plurality of temperatures sensors and means for determining a position of each one of said sensors within the cross-section of said conduit;

generating a map of said temperature within the cross-section of said conduit;

applying current pulses to said temperature sensors to momentarily raise the temperature of said sensors;

determining the thermal transient response at each sensor, thereby determining heat transfer properties of fluid in which each one of said temperature sensors is immersed;

generating a map of said heat transfer properties within the cross section of said conduit; and comparing said thermal transient map and said temperature map with similar maps of known flow regimes of fluids thereby determining said flow regime in said conduit, wherein said maps of known flow regimes are generated from laboratory experiments in a flow loop.

8. The method as defined in claim 7 wherein said step of generating a temperature map comprises generating an isothermal contour plot.

9. The method as defined in claim 7 wherein said step of generating a temperature map comprises generating an isothermal color plot.

10. A method of determining activity of perforations in a casing of a wellbore penetrating an earth formation comprising the steps of:

measuring temperature in said wellbore at known spaced apart locations within the cross-sectional area of said wellbore using a tool having a plurality of temperature sensors and means for determining a position of each one of said sensors within the cross-section of said wellbore, said step of measuring performed while fluid is flowing into said wellbore from said earth formation; and generating a first temperature map of said casing from measurements of temperature with respect to position within the cross-section of said casing made during said step of measuring;

repeating said step of measuring while said wellbore is shut-in;

generating a second temperature map from measurements made while said well bore is shut-in; and comparing said first temperature map with said second temperature map thereby determining active and inactive perforations, wherein said active perforations indicate differences in temperature distribution between said maps made while said wellbore is flowing and said maps made while said wellbore is shut in, said inactive perforations indicate no differences in said temperature distribution between said maps made while said wellbore is flowing and said maps made while said wellbore is shut in.

11. A method of determining distribution of phases and components of fluids in a multi-phase, multi-component fluid mixture flowing in a conduit comprising the steps of:

measuring temperature of said fluids in said conduit at known spaced apart locations within the cross-sectional area of said conduit using a tool having a plurality of temperature sensors and means for determining a position of each one of said sensors within the cross-section of said conduit; and generating a temperature map of said conduit and comparing said map with maps of known fluid phase and component distributions thereby determining said distribution of fluids, wherein said maps of known fluid phase and component distributions are generated from laboratory experiments in a flow loop.

12. The method as defined in claim 11 wherein said step of generating a temperature map comprises generating an isothermal contour plot.

13. The method as defined in claim 11 wherein said step of generating a temperature map comprises generating an isothermal color plot.

14. A method of determining fluid phase and component distribution in a multi-phase, multi-component fluid mixture flowing in a conduit comprising the steps of:

measuring temperature of said fluids in said conduit at known spaced apart locations within the cross-sectional area of said conduit using a tool having a plurality of temperature sensors and means for determining a position of each one of said sensors within the cross-section of said conduit;

generating a map of temperature within the cross-section of said conduit;

applying current pulses to said temperature sensors to momentarily raise the temperature of said sensors;

determining the thermal transient response at each sensor, thereby determining heat transfer properties of fluid in which each one of said temperature sensors is immersed;

generating a map of said heat transfer properties within the cross section of said conduit; and determining said fluid phase and component distribution in said conduit by comparing said thermal transient map and said temperature map with similar maps of known fluid phase and component distributions, wherein said maps of known fluid phase and component distributions are generated from laboratory experiments in a flow loop.

* * * * *